United States Patent [19]
Laroussi

[11] Patent Number: 5,876,663
[45] Date of Patent: Mar. 2, 1999

[54] STERILIZATION OF LIQUIDS USING PLASMA GLOW DISCHARGE

[75] Inventor: Mounir Laroussi, Knoxville, Tenn.

[73] Assignee: The University of Tennessee Research Corporation, Knoxville, Tenn.

[21] Appl. No.: 747,091

[22] Filed: Nov. 12, 1996

Related U.S. Application Data

[60] Provisional application No. 60/006,700, Nov. 14, 1995.

[51] Int. Cl.$^6$ .......................... A23L 3/3409; A61L 2/14; C02F 1/00
[52] U.S. Cl. .......................... 422/23; 422/21; 422/22; 422/28; 422/41; 204/164; 426/237; 210/764; 428/224; 315/111.21
[58] Field of Search .................. 204/164; 422/21, 422/22, 23, 28, 41; 426/237; 210/764; 315/111.21; 428/224

[56] References Cited

U.S. PATENT DOCUMENTS

| | | |
|---|---|---|
| 3,772,188 | 11/1973 | Edwards . |
| 4,348,357 | 9/1982 | Bithell . |
| 4,801,427 | 1/1989 | Jacob . |
| 4,957,606 | 9/1990 | Juvan ............................ 204/164 |
| 5,026,484 | 6/1991 | Juvan ............................ 210/717 |
| 5,387,842 | 2/1995 | Roth et al. . |
| 5,403,453 | 4/1995 | Roth et al. . |
| 5,414,324 | 5/1995 | Roth et al. . |
| 5,456,972 | 10/1995 | Roth et al. . |
| 5,707,594 | 1/1998 | Austin . |

OTHER PUBLICATIONS

Ku, Yongmin et al., "Surface Cleaning of Metals in Air With a One Atmosphere Uniform Glow Discharge Plasma", *2nd IEEE Int. Conference on Plasma Science*, Madison, Wisconsin, Paper 6DP09 (Jun. 5–8, 1995).

Laroussi, Mounir, "Serilization of Contaminated Matter with an Atmospheric Pressure Plasma", IEEE Trans. on Plasma Science, vol. 24, No. 3 (Jun., 1996).

Roth, J.R. et al., "Experimental Generation of a Steady-State Glow Discharge at Atmospheric Pressure", *1992 (19th) IEEE Int. Conference on Plasma Science*, Conference Record–Abstracts, Paper 5P–21, IEEE Catalog No. 92–TH0460–6, ISBN 0–7803–0716–X, pp. 170–171, Tampa, FL (Jun. 1–3, 1992).

*Primary Examiner*—James C. Housel
*Assistant Examiner*—Phuong T. Bui
*Attorney, Agent, or Firm*—Weiser and Associates, P.C.

[57] ABSTRACT

A method and apparatus are disclosed for sterilization of liquids using a steady-stage glow discharge apparatus, at one atmosphere.

14 Claims, 6 Drawing Sheets

5,876,663

STERILIZATION OF LIQUIDS USING PLASMA GLOW DISCHARGE

This application claims the benefit of U.S. provisional application No. 60/006,700, filed Nov. 14, 1995.

This invention relates to the sterilization of liquids, such as infectious waste, by plasma irradiation.

BACKGROUND OF THE INVENTION

U.S. Pat. No. 5,414,324, discloses a steady-state glow discharge plasma apparatus operated at one atmosphere of pressure between a pair of spaced apart insulated metal plate electrodes, and R.F. energized with an rms potential of 1 to 5 KV at 1 to 100 KHz. Air or other gases fill the space between the electrodes. The electrodes are charged by an impedance matching network adjusted to produce the most stable uniform glow discharge. That patent is incorporated herein by reference.

Other patents that relate to steady-state glow discharge plasma at one atmosphere are U.S. Pat. Nos. 5,387,842, 5,456,972 and for the treatment of polymer material 5,456,972. These patents are incorporated herein by reference.

SUMMARY OF THE INVENTION

In one embodiment the invention is a method for sterilizing a liquid, that is for killing the microorganisms present in a liquid, which method comprises exposing the liquid to a steady state glow plasma discharge for a period of time sufficient to kill or render inviable all microorganisms present in the liquid. Preferably, the glow plasma discharge is at a pressure of about one atmosphere.

In another embodiment, the invention is an apparatus for sterilizing a liquid, which apparatus comprises a pair of metal plate electrodes mounted in approximately face-to-face parallel alignment, a radio frequency (RF) power amplifier connected to both plates energized with an rms potential of 1 to 5 or more KV at 1 to 100 KHz, an enclosure for maintaining a controlled gas atmosphere in the space between the plates, and a container positioned within the enclosure and between the plates for holding the liquid to be sterilized, which liquid may be stationary within the container or may flow through the container.

DESCRIPTION OF THE PREFERRED EMBODIMENT

Figure 1:
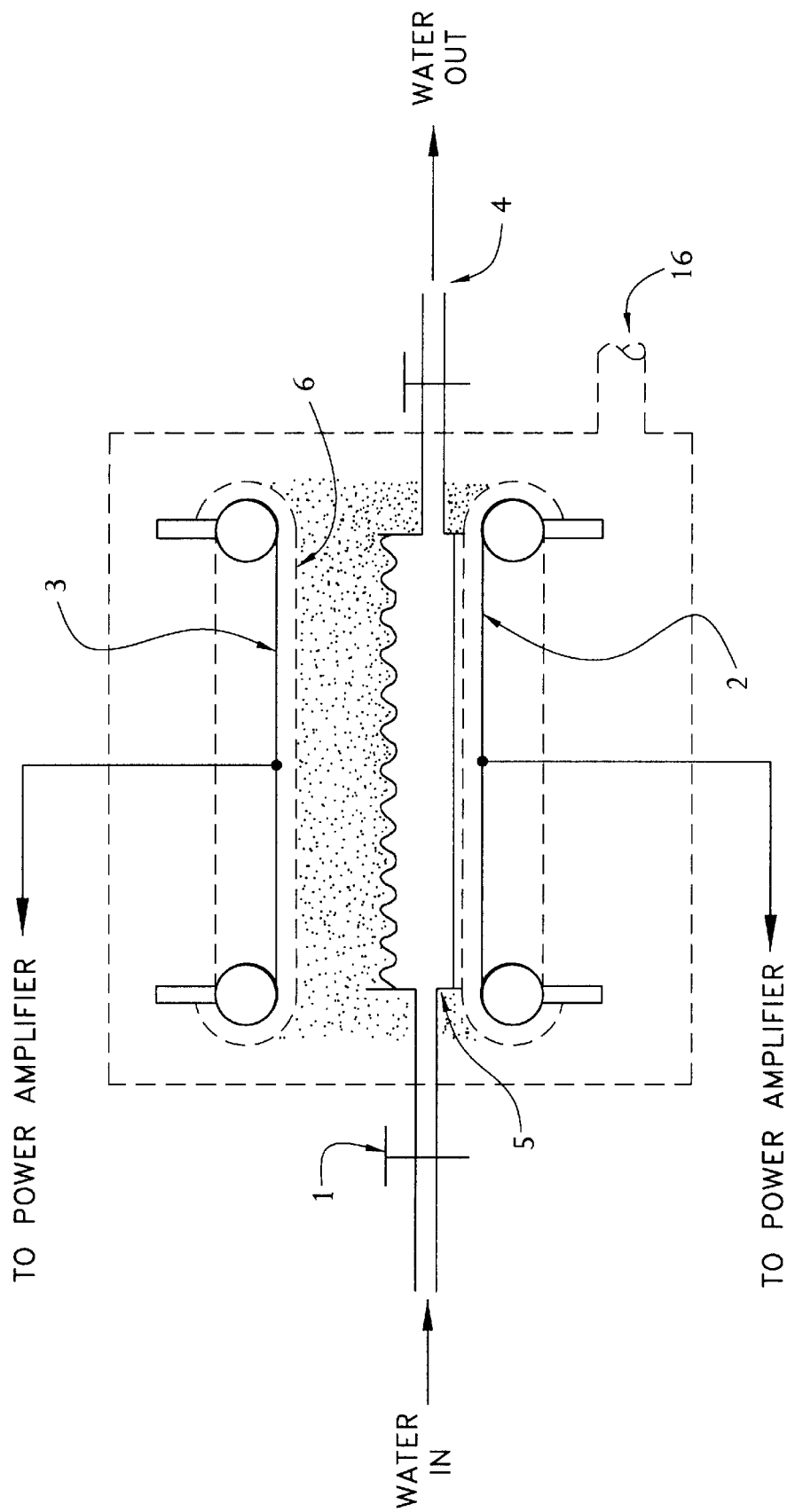
FIG. 1 shows a schematic of the apparatus for practicing the method of the invention.

In accordance with the invention, the apparatus described is used to irradiate, by a steady-state glow discharge plasma, infectious waste for sterilization. Liquids, like water, can be exposed to the plasma and treated in accordance with the method of the invention. Thus, health threatening organisms living in liquids for human or animal consumption can be exterminated by exposure of the liquid to the one atmosphere pressure plasma. In effect, this brings about the elimination or sterilization of unsafe organisms from the liquids, like from water supplies.

In such manner, water treatment systems of municipalities and other locations can be treated and sterilized. The method of the invention is more attractive, both economically and environmentally, than the present methods of incineration. Excellent commercial applicability is expected.

The apparatus for production of the plasma discharge comprises an enclosure, such as a plexiglass enclosure, which contains two electrodes, either both insulated or one of the two, preferably the lower electrode, uninsulated, which are separated by a variable distance d. The plasma is generated by applying an RF voltage between the two electrodes. When the frequency of the RF voltage falls within a range around a critical frequence $f_o$ a uniform glow discharge fills the entire space between the electrodes. The critical frequency $f_o$ is determined by the equation: $f_o = e V rms/\pi m v_c d^2$, where Vrms is the rms value of the voltage between the two electrodes, $v_c$ is the collision frequency (dominated by electron-neutral collisions and is about $10^{12}$ Hz for electrons and $10^{10}$ HZ for ions), and d is the distance between the electrodes. The rms voltage necessary to start the discharge depends on the type of gas between the electrodes and the distance d. For an inert gas like helium and a 1 to 5 cm gap between the electrodes, $f_o$ is about 1 to about 10 KHz. In the expression of $f_o$ shown above, "e" is the electronic charge, ($1.6 \times 10^{-19}$ C) and "m" is the atomic mass of the gas.

Virtually any liquid can be sterilized by the method of the invention. The liquid to be sterilized may be of low viscosity, such as water, or of high viscosity, such as a gel. Generally, any liquid which can be maintained at a depth of 1 cm or less may be sterilized by the method of the invention. The method of the invention is particularly well suited for the sterilization of liquids such as water, milk, juice, beer, pharmaceutical solutions and suspensions, blood and blood products, microbiological culture media, and sewage.

The method of the invention can be used to sterlze a liquid containing one or more microorganisms. The method is effective to kill virtually any microorganism, at any stage of growth of the microorganism. Examples of microorganisms which may be destroyed in accordance with the method of the invention include viruses, gram negative bacteria such as Pseudomonas spp. and *Escherichia coli*, gram positive bacteria such as *Staphylococcus aureus*, and Bacillus spp., including bacillus endospores, and eukaryotic microorganisms, such as protozoa, yeasts, and fungi, including endospores thereof.

Generally, in accordance with the method of the invention, a liquid to be sterilized is placed within a container, and the container is immersed in a steady state plasma glow discharge for a period of time sufficient to kill the microorganisms in the liquid. Typically an exposure time between 10 seconds and 10 minutes is sufficient to sterilize a liquid. The depth of liquid within the container should be less than about 1 cm, such as about 0.1 or 0.2 to 0.7 cm, and preferably between about 0.3 to 0.5 cm. The container may be any container which is of a size to fit within the gap between the two electrodes which produce the plasma glow discharge and which is made of a dielectric material which can withstand the plasma power density without sustaining severe damage, such as breaking or developing a leak. Examples of suitable materials for containers include glass, plexiglass, ceramic, hard plastics, and crystal such as quartz.

The method of the invention to sterilize a stationary liquid maintained within a container comprises the following steps:
- adjusting, if necessary, the relative position of the two electrodes to accommodate the container,
- placing the container between the two plate electrodes, such as directly upon the lower electrode,
- allowing a noble gas, noble gas mixture, or mixture of air and a noble gas to occupy the sealed space between the electrodes, at a pressure of about one atmosphere, and
- applying the RF power to produce a plasma glow discharge for a time sufficient to sterilize the liquid.

Alternatively, a non-sterile liquid may be allowed to flow between the two electrodes at a flow rate such that the microorganisms in the liquid are exposed to the plasma glow discharge for a time sufficient to be killed.

The method of the invention to sterilize a flowing liquid which is not maintained stationary within a container comprises the following steps:
- allowing a gas comprising a noble gas, a noble gas mixture, or a mixture of air and a noble gas to occupy the space between the electrodes, which gas is maintained at a pressure of about one atmosphere,
- applying the RF power to produce a plasma glow discharge, and
- allowing the liquid to flow between the electrodes at a rate at which the microorganisms are exposed to the plasma glow discharge for a time sufficient to be killed. Generally, the liquid is permitted to flow within the apparatus by the operation of intake and outlet fluid valves at either side of the apparatus, which valves are opened to provide a constant flow rate between the valves.

If desired, a sterile container may be positioned to receive the sterile treated liquid flow from the outlet valve.

Following treatment, sterility of the treated liquid may be determined by the absence of microbial growth. For example, the treated liquid may be incubated in conditions suitable for growth of the microorganism, i.e. with nutrient media at physiological growth temperatures, for 24 to 48 hours to verify the absence of bacterial growth by the lack of turbidity in the liquid. Up to one to two weeks incubation may be necessary to verify the absence of fungal growth.

Alternatively, the liquid may be examined microscopically to determine sterility. Because the plasma treatment destroys the integrity of the microbial structure, no intact microbial cells remain following effective treatment, with only fragments of organic debris being detectable.

The operational parameters employed in the method of the invention generally are interrelated, with individual parameters being affected by changes in other parameters. In general, the parameters are as follows.

The power density of the apparatus is generally between 50 and 80 mw/cc, at which power the liquid which is treated will not be destroyed or evaporated. If partial or total destruction of the liquid is tolerable or desired, higher power densities may be employed, such as from 50 mw/cc up to about 300 mw/cc. The RMS voltage of the apparatus of the invention may be from 1 to 10 kV. The frequency may be from 1 to 50 kHz, preferably between 1 and 10 kHz, and most preferably between 1 and 5 kHz. The gap between the electrodes can be from near zero, to about 5 cm, preferably between about 0.3 and 2.0 cm.

Virtually any gas may be used to form the plasma. Preferably, an inert gas, such as the noble gases helium, argon, or neon, alone or in a gas mixture, is used. Air may be used, alone or in mixture with a noble gas, in any ratio between about 99:1 and 1:99. In a most preferred embodiment, the gas mixture comprises oxygen, which appears to contribute to lethality of the plasma. Non-inert gases, such as $CO_2$, $NO_2$, or $H_2O_2$, may also be used, although the use of non-inert gases will generally necessitate the use of higher voltages or a smaller gap.

The depth of liquid between the two electrodes at a power density below about 80 to 100 mw/cc should generally be about one centimeter or less, such as in a thin film of liquid, or between 0.1 to 0.7 cm. Preferably, the depth of liquid is about 0.3 to about 0.5 cm. At a power density of higher than about 100 mw/cc, the depth of the liquid may be up to about 2.0 cm.

The flow rate may be varied depending on the microorganisms in the liquid which are to be killed, the depth of the liquid, the power density of the plasma glow discharge, and the surface area of the plates. Generally, flow rates between 200 $\mu$l/sec and 10 ml/sec are suitable to sterilize a liquid. A suitable flow rate may be determined by routine experimentation whereby all parameters except flow rate are maintained constant and the flow rate at which no microorganisms survive exposure to the plasma glow discharge is determined. For example, in a system with a power density of 50–80 mw/cc, 25×25 cm plates, 0.5 cm depth of liquid nutrient broth, and a non-spore forming microorganism, such as a Pseudomonas or a protozoan, a flow rate of about ⅓ liter per minute, resulting in an average exposure time of about 20 seconds, is sufficient. For spore forming microorganisms, such as bacillus or coccidia which are harder to kill than non-spore formers, the flow rate needed to sterilize may be lower, such as ¼ to ¹⁄₁₀ liter per minute.

One skilled in the art will understand that the above parameters are interrelated and will be able to select appropriate values of these parameters based on the teaching of this specification. For example, one skilled in the art will understand that a larger plate surface will permit a correspondingly higher flow rate with no decrease in exposure time. As another example, where the plasma forming gas comprises a large percentage of inert gases which are easily induced to form a plasma, a voltage of 1 kV may be adequate, whereas with a gas consisting of non-inert gases, such as air, a voltage of 10 kV may be used.

FIG. 1 shows the treatment of a water supply which is contaminated with undesired microscopic microorganisms, like bacteria. The water supply controlled by a valve 1 is supplied to the space between the two electrodes 2, 3 and exits at the outlet 4 after exposure and sterilization to the plasma irradiation. The water is supplied as a thin layer into a container 5 positioned between the two electrodes equipped with a glass cover 6. The water is exposed to irradiation for a period long enough to be sterilized.

Figure 2:
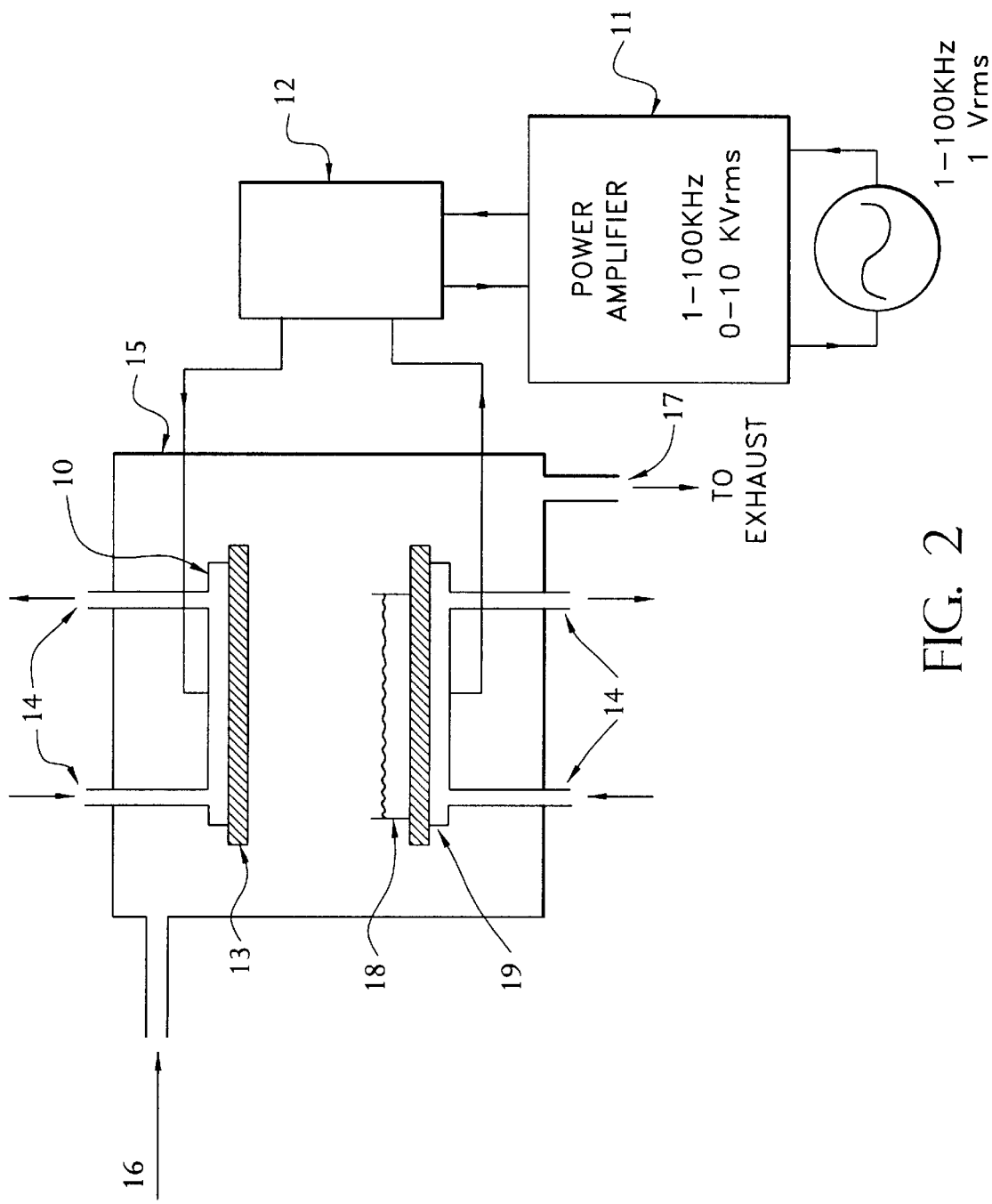
FIG. 2 shows a schematic of the apparatus for sterilizing a static liquid within a container.

FIG. 2 shows an apparatus for sterilization treatment of a non-flowing liquid in a container. The electrodes 10 are connected to a power amplifier 11, optionally through an impedance matching network 12. The electrodes 10 are covered by a dielectric insulation 13, and are cooled by a water flow circuit 14. Surrounding the assembly is an enclosure or environmental isolation barrier 15 for maintaining a controlled gas atmosphere in the volume between the electrode plates 10. A gas inlet 16 and outlet 17 are present to permit entry and removal of gas from the enclosure 15. The sample to be treated is contained within a container 18 which may rest upon the lower electrode 19.

Figure 3:
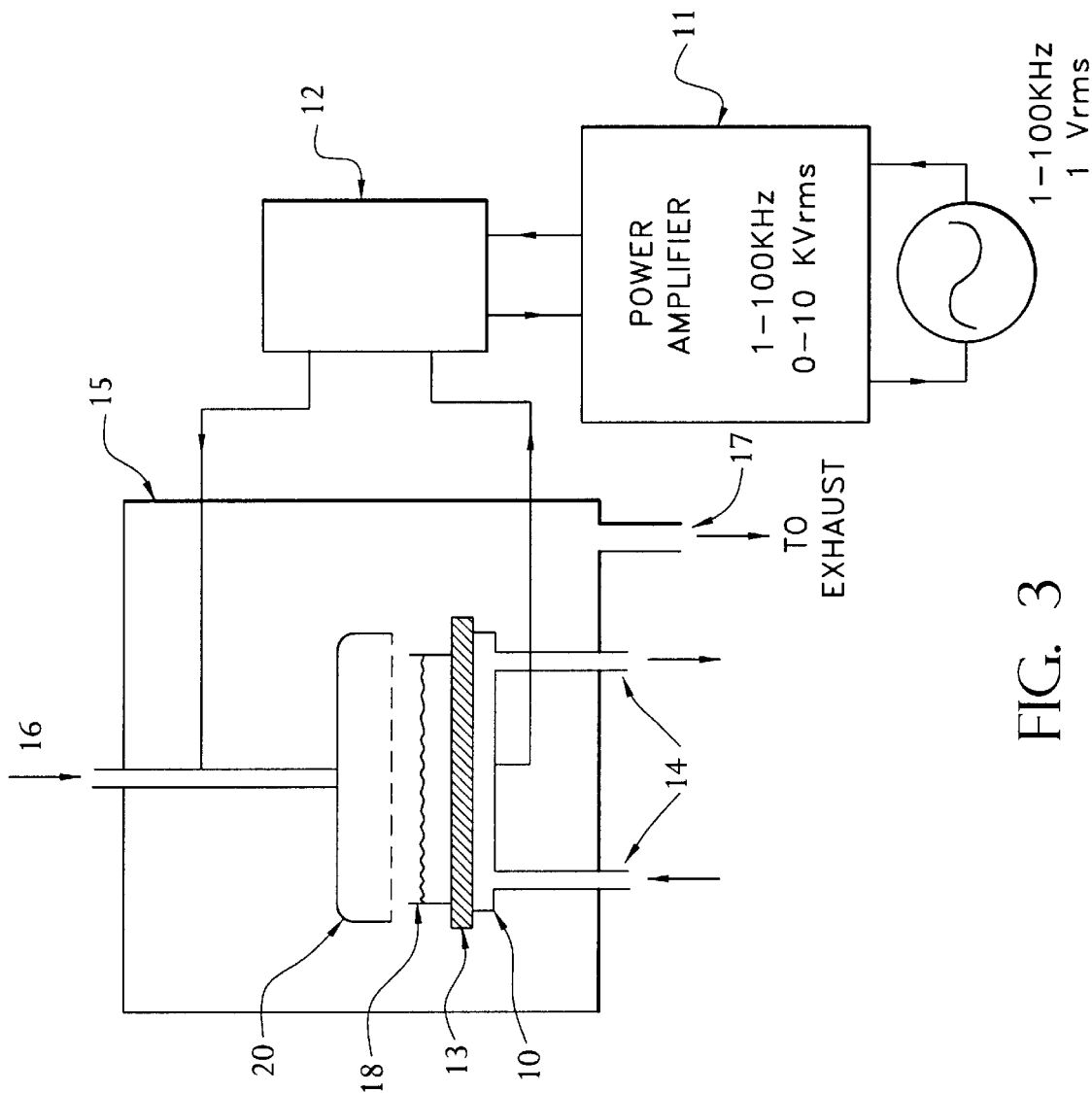
FIG. 3 shows a schematic of the apparatus for sterilizing a liquid in which one of the electrodes is perforated.

FIG. 3 shows an alternative embodiment of the apparatus of the invention, in which the gas inlet 16 is connected directly to one of the electrodes 10, such as the upper electrode as shown, and this electrode is perforated 20 to allow entry of the gas in the space between the electrodes. The perforated electrode is not insulated. Perforations in the electrode are generally homogenously distributed across the surface of the electrode and are 1 to 2 mm in diameter, with the distance between holes being greater than the diameter of the holes. The perforations permit the production of a spatially uniform plasma and, if the above conditions are met, the actual number of holes in the electrode is of little importance.

Figure 4:
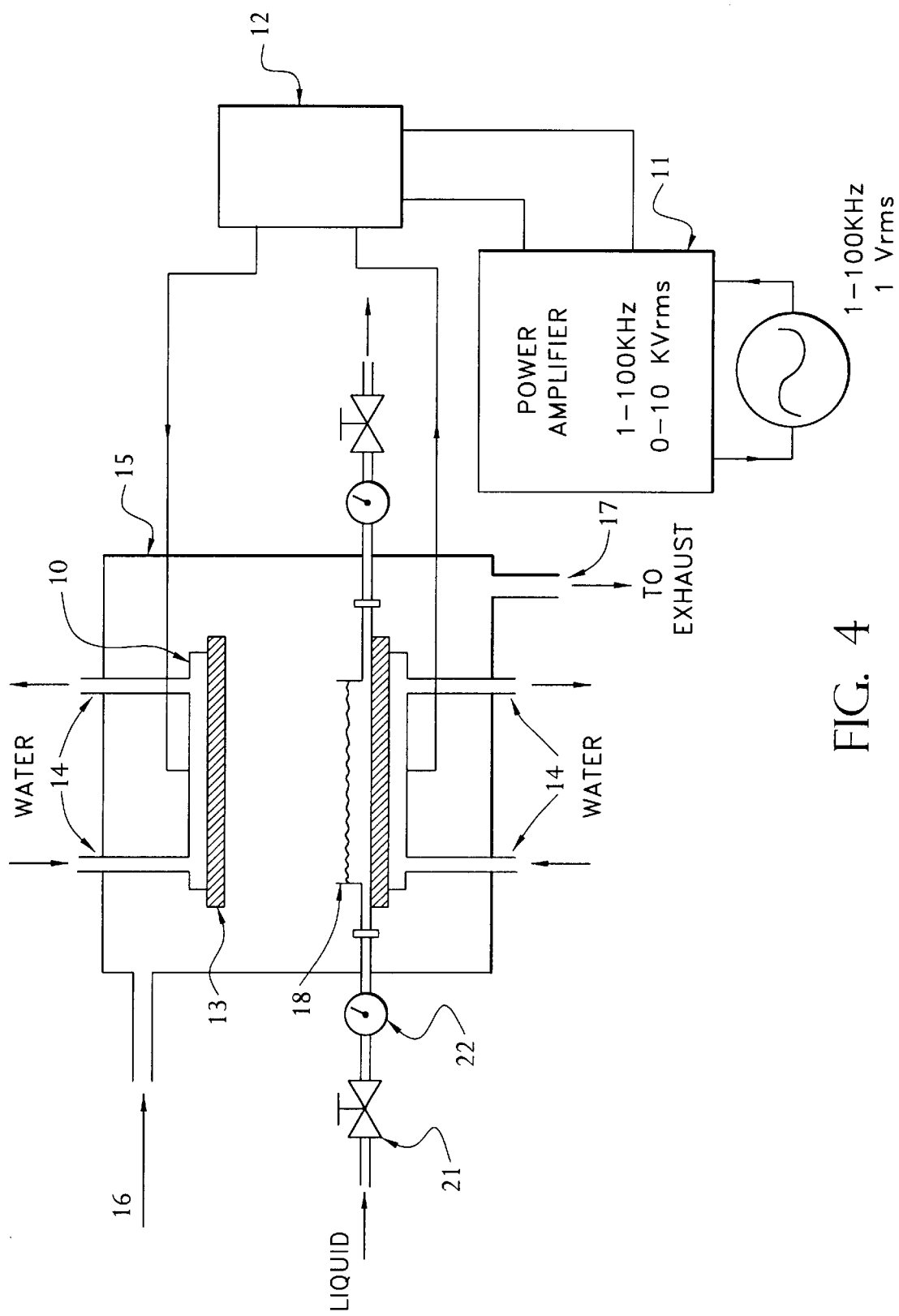
FIG. 4 shows a schematic of the apparatus for sterilizing a flowing liquid.

FIG. 4 shows an alternative embodiment of the apparatus of the invention, in which the liquid to be treated flows in the space between the electrodes. Inlet and outlet valves 21 regulate flow of water through the container 18 which is positioned in the space between the electrodes 10. Flowmeters 22 are positioned between the container 18 and the valves 21 to match the inflow and outflow rates of the liquid.

Figure 5:
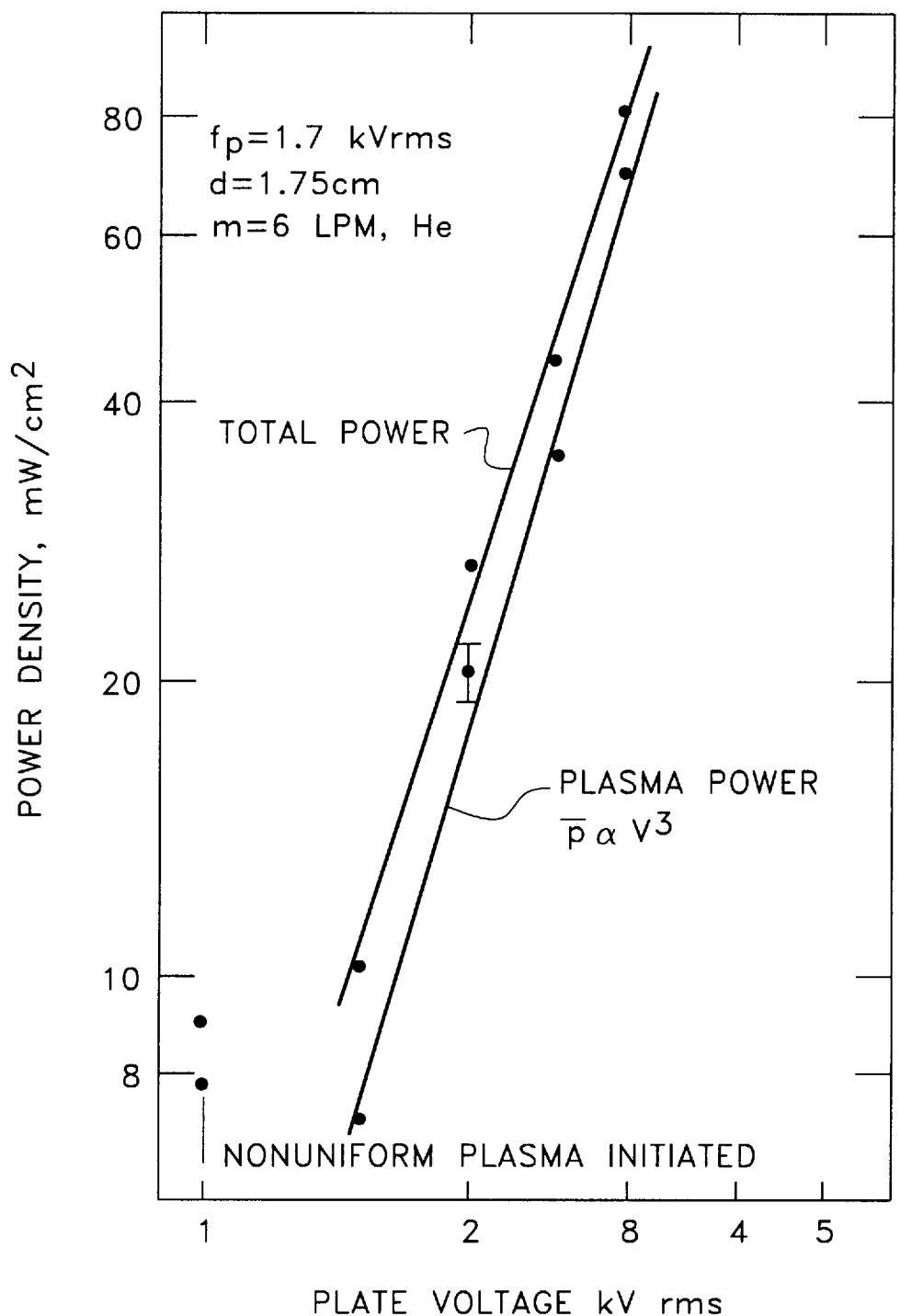
FIG. 5 is a log-log graph of total and plasma power density in milliwatts per cubic centimeter as a function of RMS voltage applied to the electrodes.

The plasma power is proportional to the production rate of active species in the plasma; the reactive power determines the required power handling rating of the plasma power supply and associated equipment. The total power is the sum of plasma and reactive power. FIG. 5 shows a log-log plot of the plasma and total power density in milliwatts per cubic centimeter, as functions of the RMS voltage applied to the parallel electrode plates.

Figure 6:
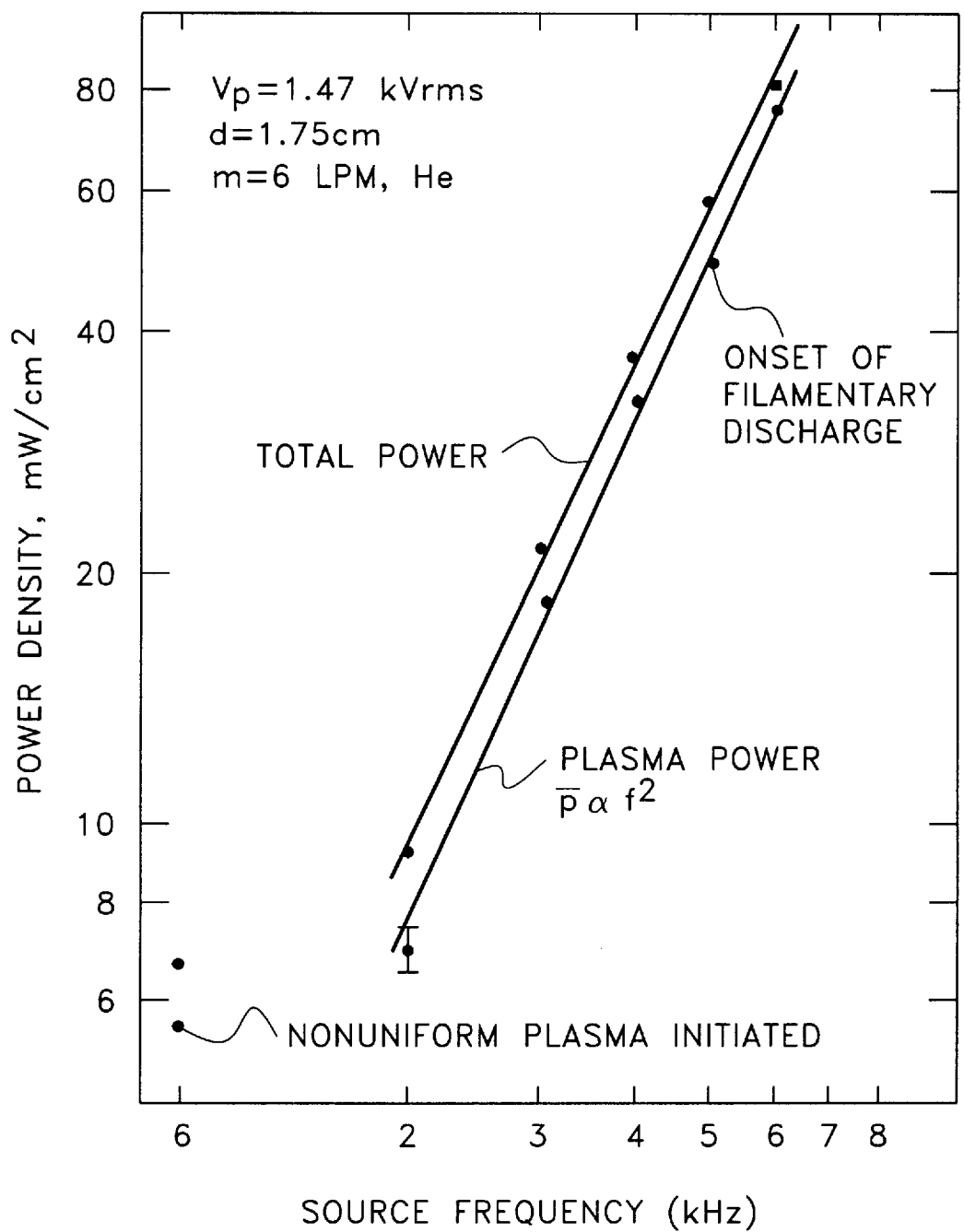
FIG. 6 is a log-log graph of total and plasma power density in milliwatts per cubic centimeter, as a function of R.F. frequency.

FIG. 6 is a similar representation of the power density plotted on log-log coordinates as a function of the frequency. The approximate bound of the uniform plasma discharge regime is shown by the arrow. These data were taken in helium gas for the same plasma volume and electrode separation as FIG. 5.

In the apparatus, the distance between the two electrodes can be varied from a few millimeters to a few centimeters. The metal of the electrodes can be of any good conductor, such as copper, aluminum, etc. The insulation of the electrodes is a glass cover, 2 ml. to 5 ml. thick, as needed. Any dielectric material capable of withstanding the plasma power density may be used as an insulation of at least one of the electrodes. The electrodes are connected to an RF source (of a few KHz frequency, and of 1 to a few KV voltage) and an inert gas such as helium or argon is introduced into the enclosure. A plasma is generated between the two electrodes. The generation of a plasma in a one atmosphere environment is disclosed in U.S. Pat. Nos. 5,414,324, 5,387,842, and 5,456,972, which are incorporated herein by reference.

When the liquid is being irradiated by the plasma, its surface is constantly bombarded by free radicals, excited atoms or molecules, electrons, ions and radiation which kill a large number of the living microorganisms which are on the surface of the liquid. In accordance with the method of the invention, the exposure time is adjusted to cause the sterilization of the liquid and can vary from a few tens of seconds to several minutes, such as 1–5 minutes to several tens of minutes, such as 10–30 minutes. Optimum time of exposure, at which a desired level of sterilization is to be achieved can be readily determined. The extent of sterilization is determined by standard methods. Waste water sterilized in accordance with the method of the invention, and free of infectious microorganisms will be disposed of in accordance with conventional means.

Additional information concerning sterilization of liquids by prior art methods and by the method of the present invention is disclosed in Laroussi, M., "Sterilization of Contaminated Matter with an Atmospheric Pressure Plasma", IEEE Transactions on Plasma Science, vol. 24(3) :1188–1191 (1996) , which article is incorporated herein by reference. The invention is further illustrated by the following non-limiting examples.

EXAMPLE 1

A glow discharge was generated between two plate electrodes, in which only the lower electrode was insulated. Helium gas at atmospheric pressure was introduced into the space between the electrodes. The rms voltage between the electrodes was 5 KV, and the frequency range in which a stable steady-state plasma glow discharge was obtained was between 300 Hz and 4 kHz, with a distance of about 1 cm between the electrodes.

A yeast extract polypeptone glucose (YEPG) nutrient microobial growth medium was contaminated with about $4 \times 10^6$ cfu/ml of *Pseudomonas fluorescens* bacteria. About 15 ml of the contaminated YEPG medium was placed in a petri dish which was placed between the electrodes of the apparatus and subjected to the plasma glow discharge for 10 minutes. After 10 minutes, a 100 $\mu$l sample of the treated medium was placed in a test tube containing 9.9 ml of a sterile phosphate buffer, which was then incubated for 48 hours at 30° C. No live bacteria were detected after the incubation.

Live bacteria were found to be present in samples which were incubated in a similar manner but which were not exposed to the plasma glow discharge.

EXAMPLE 2

The procedure of Example 1 is repeated with a helium-air gas mixture. No live bacteria are detected in the medium after treatment with the plasma.

EXAMPLE 3

The procedure of Example 1 is repeated with air as the plasma producing gas mixture. No live bacteria are detected in the medium after treatment with the plasma.

One skilled in the art will understand that various modifications can be made to the invention as disclosed herein without departing from the scope of the invention. These modifications are intended to be covered in the following claims.

What is claimed is:

1. A method for sterilization of a liquid which contains microorganisms which comprises directly exposing the liquid to the plasma of a steady-state glow plasma discharge at a pressure of about one atmosphere and permitting the liquid to remain exposed to the plasma discharge for a time sufficient to kill microorganisms within the liquid, wherein the steady-state glow plasma discharge is generated using electrodes R.F. energized with an rms potential of about 1 to 5 KV at about 1 to 100 KHz.

2. The method of claim 1 wherein the microorganisms are selected from the group consisting of viruses bacteria, protozoa, yeast, and fungi.

3. The method of claim 2 wherein the microorganisms are pathogenic microorganisms.

4. The method of claim 2 wherein the liquid is exposed to the plasma discharge for a time between 10 seconds and 20 minutes.

5. The method of claim 1 wherein the liquid is a non-flowing liquid.

6. The method of claim 1 wherein the liquid is a flowing liquid.

7. The method of claim 1 wherein the depth of the liquid as it is exposed to the plasma discharge is between about 0.1 cm and 2 cm.

8. The method of claim 1 wherein the liquid to be sterilized is selected from the group consisting of water, milk, juice, beer, pharmaceutical solutions and suspensions, blood and blood products, microbiological culture media, and sewage.

9. The method of claim 1 wherein the plasma is generated by an apparatus which comprises a pair of insulated metal plate electrodes, at least one of which is insulated, which are spaced between about 0.1 and 5 cm apart in a gas selected from the group consisting of air, nitrous oxide, carbon dioxide, hydrogen peroxide, a noble gas, and mixtures thereof.

10. The method of claim 3 in which the pathogenic microorganisms are gram negative bacteria.

11. The method of claim 3 in which the pathogenic microorganisms are gram positive bacteria.

12. The method of claim 1 in which the liquid is a low viscosity liquid.

13. The method of claim 1 in which the liquid is a high viscosity liquid.

14. The method of claim 13 in which the high viscosity liquid is a gel.

* * * * *